US008414814B2

United States Patent
Su et al.

(10) Patent No.: US 8,414,814 B2
(45) Date of Patent: Apr. 9, 2013

(54) TEMPORAL INTRALUMINAL STENT, METHODS OF MAKING AND USING

(75) Inventors: Shih-Horng Su, Irvine, CA (US); Debashis Dutta, Irvine, CA (US)

(73) Assignee: Biosensors International Group, Ltd., Hamilton (BM)

( * ) Notice: Subject to any disclaimer, the term of this patent is extended or adjusted under 35 U.S.C. 154(b) by 42 days.

(21) Appl. No.: 12/897,463

(22) Filed: Oct. 4, 2010

(65) Prior Publication Data

US 2011/0106236 A1 May 5, 2011

Related U.S. Application Data

(63) Continuation of application No. 11/693,684, filed on Mar. 29, 2007, now abandoned.

(60) Provisional application No. 60/862,939, filed on Oct. 25, 2006.

(51) Int. Cl.
*B28B 1/38* (2006.01)

(52) U.S. Cl.
USPC .......... 264/305; 264/215; 264/241; 264/279; 264/294; 264/319; 264/320; 264/306; 264/308; 264/533; 264/563; 264/301; 264/303; 264/304; 264/307; 264/235; 264/346; 264/291; 264/292; 264/154; 264/162; 264/400; 264/171.12; 264/171.27; 264/212; 264/632; 264/635; 264/642; 264/510; 264/511; 264/512; 427/2.24; 427/2.25; 427/2.1; 427/2.3; 623/1.11; 623/1.12; 623/1.13; 623/1.14; 623/1.15; 623/1.17; 623/1.2; 623/23.7

(58) Field of Classification Search .................. 264/305, 264/306, 308, 310, 311, 312, 533, 560, 563, 264/632, 635, 642, 447, 448, 87, 510, 511, 264/512, 515, 171.26, 171.27, 177.14, 212, 264/215, 241, 294, 235, 346, 341; 623/1.11–1.17, 623/1.2, 23.7, 900
See application file for complete search history.

(56) References Cited

U.S. PATENT DOCUMENTS

| | | | |
|---|---|---|---|
| 4,661,300 A * | 4/1987 | Daugherty | 264/40.6 |
| 5,423,754 A * | 6/1995 | Cornelius et al. | 604/103 |
| 6,153,252 A * | 11/2000 | Hossainy et al. | 427/2.3 |
| 2003/0004563 A1* | 1/2003 | Jackson et al. | 623/1.15 |
| 2004/0000046 A1* | 1/2004 | Stinson | 29/426.4 |
| 2004/0199242 A1* | 10/2004 | Hong et al. | 623/1.16 |

* cited by examiner

*Primary Examiner* — Jeffrey Wollschlager
*Assistant Examiner* — Stella Yi
(74) *Attorney, Agent, or Firm* — Kilpatrick Townsend & Stockton LLP

(57) ABSTRACT

A biodegradable polymer stent with radiopacity and a method of making and using a stent with enhanced mechanical strength and/or controlled degradation for use in a bodily lumen is described.

6 Claims, 14 Drawing Sheets

TEMPORAL INTRALUMINAL STENT, METHODS OF MAKING AND USING

CROSS-REFERENCE TO RELATED APPLICATIONS

This application claims the benefit of U.S. Provisional Application No. 60/862,939 filed Oct. 25, 2006, which is incorporated herein by reference.

TECHNICAL FIELD

The present application relates to a biodegradable polymer stent with radiopacity and a method of making and using the stent.

BACKGROUND

A stent is an endoprosthetic implant, generally tubular in shape, typically having an open or latticed tubular construction which is expandable to be inserted into an anatomical lumen to provide mechanical support to the lumen and to maintain or to re-establish a flow channel within said lumen. Stents are known for use in blood vessels such as the aorta, carotid artery, or coronary artery or arteries, to treat arterial blockage or aneurysm, for example. In additions, stents are known for use in maintaining patency of body lumens or channels besides blood vessels; these include bile duct stents, urethral stents, and the like. As an example, an endovascular stent may be inserted into a blood vessel during angioplasty, and is designed to prevent early collapse of a vessel that has been weakened or damaged by angioplasty. Insertion of endovascular stents has been shown to reduce negative remodeling of the vessel while healing of the damaged vessel wall proceeds over a period of months.

During the healing process, inflammation caused by angioplasty and stent implant injury often causes smooth muscle cell proliferation and regrowth inside the stent, thus partially closing the flow channel, and thereby reducing or eliminating the beneficial effect of the angioplasty/stenting procedure. This process is called restenosis. Blood clots may also form inside of the newly implanted stent due to the thrombotic nature of the stent surfaces, even when biocompatible materials are used to form the stent. While large blood clots may not form during the angioplasty procedure itself or immediately post-procedure due to the current practice of injecting powerful anti-platelet drugs into the blood circulation, some thrombosis is always present, at least on a microscopic level on stent surfaces, and it is thought to play a significant role in the early stages of restenosis by establishing a biocompatible matrix on the surfaces of the stent whereupon smooth muscle cells may subsequently migrate in and proliferate.

Stents can be of a permanent or temporary nature. Temporary stents which are made from biodegradable material may be advantageous, particularly in cases of recurrent vessel narrowing in which it is desirable to insert a subsequent stent at or near the site of initial stent placement, or where a stent is needed only temporarily to counteract post-surgical swelling that may cause obstruction of a bodily lumen, such as obstruction of the urethra after prostate surgery.

Bioabsorbable/Biodegradable/Bioerodible stents are typically made of synthetic polymers that are biocompatible and are broken down by biological means. Biodegradable stents are also known wherein the outer surfaces or even the entire bulk of polymer material is porous. For example, PCT Publication No. WO 99/07308, which is commonly owned with the present application, discloses such stents, and is expressly incorporated by reference herein.

Stents are also known which contain APIs (active pharmaceutical ingredients), which are generally intended to reduce or eliminate thrombosis or restenosis. Such APIs are often dispersed or dissolved in either a durable or biodegradable polymer matrix, which is applied as a coating over at least a portion of the filament surface. After implantation, the API diffuses out of the polymer matrix and preferably into the surrounding tissue.

A variety of agents specifically claimed to inhibit smooth muscle-cell proliferation, and thus inhibit restenosis, have been proposed for release from endovascular stents. Rapamycin (sirolimus), an immunosuppressant reported to suppress both smooth muscle cell and endothelial cell growth, has been shown to have effectiveness against restenosis, when delivered from a polymer coating on a stent (see, for example, U.S. Pat. Nos. 5,288,711 and 6,153,252). Also, PCT Publication No. WO 97/35575 and WO 2003/090684 describe the macrocyclic triene immunosuppressive compound everolimus and related compounds, which have been proposed for treating restenosis. U.S. Pat. No. 6,159,488 describes the use of a quinazolinone derivative; U.S. Pat. Nos. 6,171,609 and 5,716, 981 describe the use of paclitaxel (taxol). U.S. Pat. No. 5,288, 711 describes the use of both heparin and rapamycin. Tranilast, a membrane-stabilizing agent thought to have anti-inflammatory properties is disclosed in U.S. Pat. No. 5,733, 327. As described in U.S. Pat. No. 6,231,600, a mixture of polymer and therapeutic substance can be coated onto the surface of a stent, which is then coated with a second layer of polymer. The first layer may contain polymer mixed with a therapeutic substance and the second layer may contain polymer mixed with heparin. In U.S. Pat. No. 6,939,376, Shulze et al. disclose a stent for inhibiting restenosis, which is comprised of a stent body and a biodegradable drug-release coating which contains poly(D,L-lactide) polymer and an immunosuppressive compound which is eluted with time at the vascular site of injury. U.S. Pat. No. 6,808,536 discloses local delivery of rapamycin or its analogs from an intravascular stent, either directly from tiny micropores or channels in the stent body or mixed or bound to a polymer coating applied on stent, grooves or channels which are smaller in dimension than the stent struts. Also, U.S. Pat. No. 6,904,658 contains reference to the use of a porous plated layer to contain and elute therapeutic drug.

It is difficult to visualize non-metal, polymer based stents because they are radiolucent. Since optimal stent placement requires real time visualization to allow the cardiologist to track the stent in vivo there is a need to increase the radiopacity of non-metallic polymer based stents. Iodinated contrast media is a common type of intravenous radiographic dye containing iodine that enhances the visibility of vascular structures during radiographic procedures.

Present stents vary widely by geometry. Polymer tubular stent blanks are generally injection molded or extruded, and then die-cut, machined, or laser-cut into the desired geometry or openwork. Alternatively, rolling one or more sheets of metals or polymer may form tubular metal or polymer stent blanks. Stents may also be composed of extruded polymer filaments that are woven into a braid-like structure (see U.S. Pat. No. 6,368,346). To achieve the reticular or openwork nature of the stent body, stents generally comprise radially expandable tubular elements or "bands" which often have a zigzag or sinusoidal structure and which are interconnected by linking elements or "linkers" that typically run in a generally longitudinal direction.

Steinke (U.S. Pat. No. 6,623,521) discloses a locking stent, which may be degradable. The stent is formed from a flat sheet, or sheets, of metal or plastic and bears sliding and locking radial elements or struts. The radial elements may bear a ratcheting mechanism that permits one-way sliding of the radial elements.

U.S. Pat. No. 6,022,371 (Killion) discloses a continuous circumference tubular stent with a unitarily formed locking arm that selectively locks the stent at a desired diameter.

U.S. Pat. No. 6,540,777 (Stenzel) discloses a stent comprising a plurality of interconnected cells, at least one of which is a lockable cell with a first and second locking member which may lock with one another. Also disclosed is a stent comprising a plurality of interconnected bands with a pincer locking member extending toward an adjacent band having a tongue locking member.

U.S. Pat. No. 6,156,062 (McGuinness) discloses a stent comprising a strip of material with a groove along one edge and a tongue along the other edge, to maintain a helical configuration. No locking mechanism is disclosed.

Application Ser. No. U.S. 2004/0249442A1 (Fleming) discloses a stent comprising a lattice having a closed and an open configuration. The lattice is composed of hoops or struts that interlock with one another while moving from a closed to an open configuration, and the hoops interlock with one another by means of teeth on the struts.

U.S. Pat. No. 6,368,346 (Jadhav) discloses biocompatible and biodegradable stents made of blended polymers.

U.S. Pat. No. 5,441,515 (Khosravi) discloses a ratcheting stent comprising a cylindrical sheet having overlapping edges that interlock. The stent may be biodegradable and may be drug-releasing.

U.S. Pat. Nos. 5,817,328 and 6,419,945 disclose buffered resorbable internal fixation polymer devices for bone repair.

U.S. Pat. No. 6,932,930 discloses method to make synthetic polymer strong for stent application.

Unlike traditional metal stents, biodegradable stents are capable of bulk loading of multiple APIs and are temporary implants. Biodegradable stents, however, have typically suffered from insufficient mechanical strength and/or undesirable physical/mechanical elastic polymer recoil. In addition, the degradation time of such stents has been uncontrolled, being dependent mainly on the molecular weight of the polymer resin used. The present stents and methods provide means to adjust the polymer degradation rate and/or to enhance the mechanical strength of the polymer tube or fiber used for biodegradable stent fabrication.

SUMMARY

Figure 1:
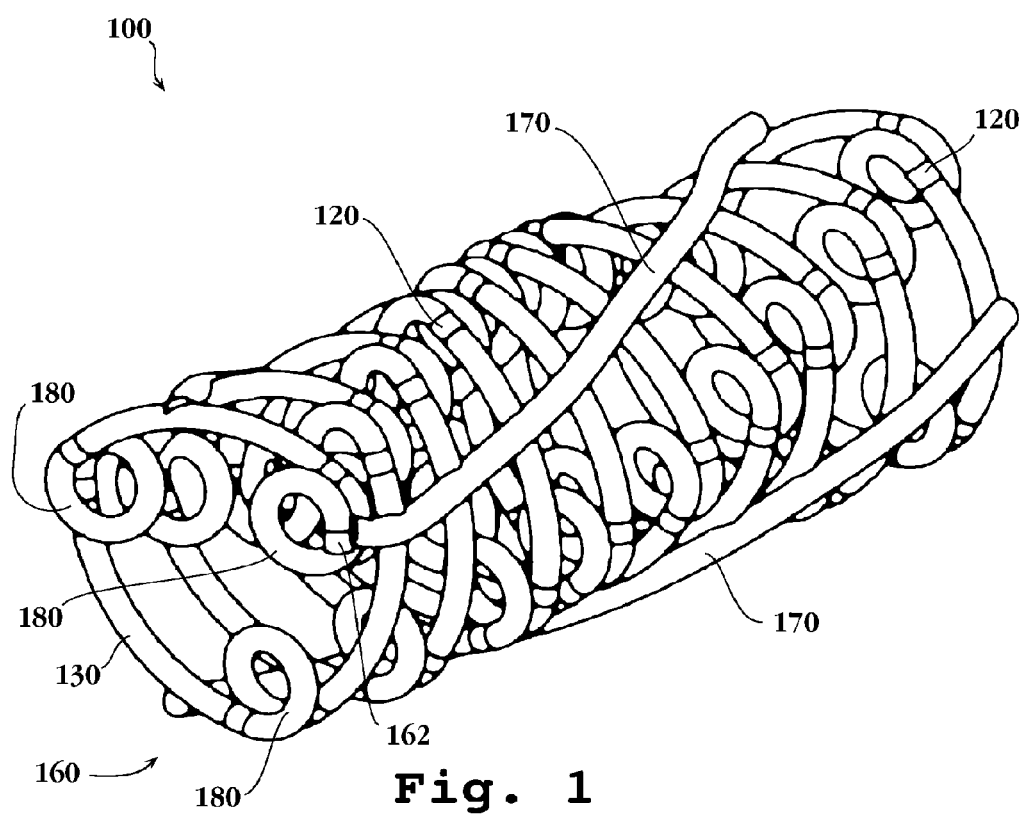
FIG. 1 is a perspective illustration of the three-dimensional structure of an expanded fiber stent.

The present stent preferably has at least one of the following features: (1) it has an all-polymer construction with similar mechanical function to conventional metallic stents; (2) it is expandable with an expansion ratio that can be customized to meet various needs; (3) it can be deployed at body temperature with low inflation pressure (3 atm); (4) it is a temporary, fully biodegradable implant; (5) it has a regulated degradation rate due to biocompatible buffers that accelerates hydrolysis; (6) it may be a local drug or gene delivery device; (7) it may be a local radiation therapy device; and (8) it can include fibers with various functions (mechanical support, acute drug burst, long-term drug release, etc.), enabling a variety of treatment options including multiple functions with a single stent and using a single stent-implant procedure.

An alternative embodiment preferably has at least one of the following features: (1) it has an all-polymer construction with similar mechanical function to conventional metallic stents; (2) it is expandable with an expansion ratio that can be customized to meet various needs; (3) it can be deployed at body temperature with low inflation pressure (3 atm); (4) it is a temporary, fully biodegradable implant; (5) it has a regulated degradation rate due to biocompatible buffers that accelerates hydrolysis; (6) it may be a local drug or gene delivery device; (7) it may be a local radiation therapy device; (8) it has enhanced mechanical strength by forming due to dip-coating and necking process; (9) it is formed at a low temperature, below the melting temperature of the polymer and right above the glass transition temperature of the polymer; and (10) it can include fibers with various functions (mechanical support, acute drug burst, long-term drug release, etc.), enabling a variety of treatment options including multiple functions with a single stent and using a single stent-implant procedure.

An alternative embodiment preferably has at least one of the following features: (1) it has an all-polymer construction with similar mechanical function to conventional metallic stents; (2) it is expandable with an expansion ratio that can be customized to meet various needs; (3) it can be deployed at body temperature with low inflation pressure (3 atm); (4) it is a temporary, fully biodegradable implant; (5) it has a regulated degradation rate due to biocompatible buffers that accelerates hydrolysis; (6) it may be a local drug or gene delivery device; (7) it may be a local radiation therapy device; (8) it can include a temporary iodinated contrast agent for increased visibility; and (9) it can include fibers with various functions (mechanical support, acute drug burst, long-term drug release, etc.), enabling a variety of treatment options including multiple functions with a single stent and using a single stent-implant procedure.

In one aspect, the stent is a temporary implant. The temporary implant permits the stress against the vessel wall to be decreased, where subsequent intervention is not necessary especially for young people and vulnerable patients, such as diabetics.

In another aspect, the stent is capable of delivering therapeutic agents incorporated in the stent body and/or coated on the polymer surface.

A further aspect of the present stent is that it is possible to vary applications and control degradation of the stent by selection of the polymer composition, the polymer molecular weight, fiber cord diameter and processing conditions, thus controlling the degradation rate, drug release rate and period of mechanical support.

An additional aspect of the present stent is that it has improved radiopacity that allows the stent to be visibly tracked during interventional procedures.

These and other aspects and advantages of the present invention will become apparent to those of ordinary skill in the art from the following detailed description of the preferred embodiment when considered in conjunction with the accompanying drawings in which like numerals in the several views refer to corresponding parts.

DETAILED DESCRIPTION OF THE INVENTION

I. Definitions

The following terms have the definitions given herein, unless indicated otherwise "Inhibiting restenosis" means reducing the extent of restenosis observed following a vascular "overstretch" injury, as measured by a reduction in average percentage of vascular stenosis at a selected time following stent placement, e.g., 1-6 months.

"Radiopaque" refers to a material that prevents the passage of electromagnetic radiation making the material fluoroscopically visible under x-rays.

II. Stents

A. Materials

The present stents are formed of one or more polymer(s) or co-polymers. In an embodiment, and as described further below, the stent body is formed of a plurality of linked tubular members by filaments. The stent body may be formed of biocompatible polymers which may be biodegradable including, but not limited to; bioresorbable, bioabsorbable, or bioerodible. A variety of natural, synthetic, and biosynthetic polymers are biodegradable. Generally, polymer backbones that contain chemical linkages such as anhydride, ester, or amide bonds, among others are biodegradable (www.sigmaaldrich.com). The mechanism for degradation is generally by hydrolysis or enzymatic cleavage of these bonds that results in division of the polymer backbone. Bioerosion of polymers generally works by conversion of the polymer that is at least partly insoluble water into one that is at least partly water-soluble. When the polymer is admixed with a therapeutic agent, as the polymer surrounding the drug is eroded, the drug is released.

In some embodiments the stent is formed of a biodegradable polymer. The rate of biodegradation may be controllable by a number of factors including, without limitation, the degree of crystallinity, the material molecular weight, and the use of biocompatible buffers which mitigate pH change at degradation site(s) and accelerate hydrolysis via dissolving pathways. In some embodiments the polymer stent releases one or more therapeutic agents, which may be released in a desired order and at a desired rate.

The use of biodegradable materials allows the stent to be decomposed and resorbed in tissues and/or be absorbed by the cells. Such materials include, but are not limited to, polymers of the linear aliphatic polyester and glycolide families, as discussed below. Other materials contemplated for the stent embodiments of the present invention include biocompatible polymers, such as of the type from the polyethylene, polyester and polypropylene families and plastics such as a polymer from the linear aliphatic polyester family. Exemplary polymers include, but are not limited to, poly(lactic acid), poly(glycolic acid) or polycaprolactone, and their associated copolymers, degradable polymers such as polyorthoester, polyanhydride, polydioxanone and polyhydroxybutyrate or combinations thereof.

Representative bio-compatible absorbable polymers include poly(lactic acid) (PLA), poly(L-lactic acid), poly(D, L-lactic acid), polyglycolic acid (PGA), poly(D-lactic -co-glycolic acid), poly(L-lactic-co-glycolic acid), poly(D,L-lactic-co-glycolic acid), poly(c-caprolactone), poly (valerolactone), poly(hydroxybutyrate), polydioxanone, poly (hydroxyl butyrate), poly(hydrovalerate), etc., including copolymers such as polyglactin (a co-polymer of lactic acid and glycolic acid (PGA-PLA)), polyglyconate (a co-polymer of trimethylene cargonate and glycolide), a co-polymer of polyglycolic acid and $\epsilon$-caprolactone, a co-polymer of poly (lactic acid) and $\epsilon$-caprolactone, poly(lactic acid)-poly(ethylene glycol) block co-polymer, and poly(ethylene oxide) -poly (butyleneteraphthalate), poly(lactic acid-co-trimethylene carbonate), poly($\epsilon$-caprolactone copolymer), poly(L-lactic acid copolymers), etc. It will be appreciated that biodegradable stents may be made from single polymers or co-polymers (for example, a co-polymer of L-lactide and $\epsilon$-caprolactone as described in U.S. Pat. No. 5,670,161 or a terpolymer of L-lactide, glycolide and $\epsilon$-caprolactone as described in U.S. Pat. No. 5,085,629. Biodegradable stents may also be formed of blended homopolymers such as those described in U.S. Pat. No. 6,368,346, including blends having similar compositions to the above copolymers. Homopolymers, blended polymers and co-polymers may have different characteristics including varying susceptibility to hydrolytic decomposition and thus may be preferred under circumstances in which faster or slower absorption is desired.

Another distinct advantage of polymer stents is that they are more compatible to MRI imaging since the polymer is not a ferromagnetic material. This property makes polymers less likely to cause signal loss during the imaging process and maintain the vessel lumen visibility. Further, subsequent analysis may be performed non-invasively.

The stents may further include a non-toxic radiopaque marker, such as, for example, barium sulfate or bismuth trioxide, into the polymer prior to stent formation, as disclosed in U.S. Pat. No. 6,368,356 to increase the radiopacity of the stents. In a preferred embodiment, the stent is coated with one or more radiopaque layers of non-ionic, water-soluble, iodinated contrast medium having a molecular weight of approximately 1 milligram (+/−20%) and a thickness of about 0.5 to 5 microns. In an embodiment, the radiopaque coating is thin and temporary as by bioabsorption. Preferably, the iodinated contrast is water-soluble for faster absorption by body tissue. Typically, the contrast media also has a low osmolality to reduce tonicity, chemical toxicity, hypersensitivity, and other potentially adverse side effects. It will be appreciated that a combination of contrast agents may be used in the same layer or in separate layers. It will further be appreciated that one or more contrast agents may be included in the stent polymer and one or more different or same contrast agents may be coated on the stent. Alternatively, the contrast media may be hydrophobic. Hydrophobic contrast media may be utilized in applications that require slower rates of degradation or excretion. Examples are disclosed in U.S. Pat. No. 7,008,614 to Kitaguchi.

Previous stents have included heavy metal coatings to confer radiopacity. These coatings, however, do not disappear once the biodegradable stents are absorbed by the tissues. The present radiopaque coatings create a biodegradable stent with temporary radiopacity without introducing permanent and harmful materials into the human body. In an embodiment, after about 2-3 minutes, there is little or no radiopaque material left in the tissues.

Contrast agents that may be used to confer biodegradable stents with radiopacity include, but are not limited to, iopamidol, iohexol, iopromide, and iodixanol. The molecular structure of these agents provides both comfort to the patient and needed visibility for the cardiologists. In general, the chemical structures consist of a hydrophobic region masked with hydrophilic regions that increase solubility and decreases binding with blood or other vascular constituents. A preferred contrast agent is iohexol.

Figure 13:
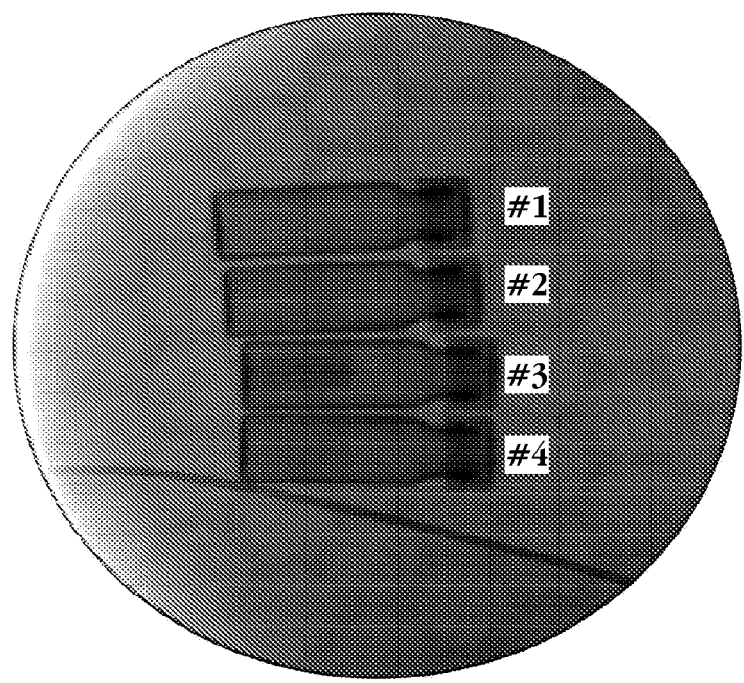
FIG. 13 is a radiograph image of a PLLA stent (#1), a stent formed of iohexol in PLLA at 26 wt. % (#2), a stent formed of iohexol in PLLA at 50 wt. % (#3), and a PLLA stent coated with iohexol (#4) and a guiding catheter.

The selected radiopaque compounds may be coated directly on a polymer stent, included within a polymer coating, impregnated within the stent structure, sandwiched between the stent and a further coating, or any combination of these techniques. Preferably, the selected radiopaque compounds are incorporated within a biodegradable polymer(s).

Where the contrast agent is coated on the stent, the agent may be formulated as a solution in a solvent such as a methanol-based solvent as described in Example 3. The solution is then applied to a stent with any appropriate method such as spraying. The solvent is evaporated to leave a thin covering of the radiopaque material over at least a portion of the stent. In a preferred embodiment, the abluminal stent surface is completely covered. The resulting stent is radiopaque under typical visualization techniques. As seen in FIG. 13 (#4), a stent coated with iohexol was visible with imaging.

The stent embodiment also optionally includes a process for combining the radiopaque compound(s) with the biodegradable polymer. The layer of contrast media can be applied by spray coating, dip-coating, co-extrusion, compress molding, electroplating, painting, plasma vapor deposition, sputtering, evaporation, ion implantation, or use of a fluidized bed. In a preferred embodiment the polymer backbone of the stent is impregnated with the contrast agent, and the drug is subsequently applied on top using one of the aforementioned processes. As described in Example 5, the contrast agent is suspended in a solution with the polymer to a desired final weight amount. As seen FIG. 13 (#2 and #3), the radiopacity of the impregnated stents appears to increase with an increase in the weight percentage of contrast agent. In an alternate embodiment, the temporary iodinated contrast agent is sandwiched between the drug on the stent backbone and a thin polymer (PLLA or other biodegradable polymer) on the abluminal surface. In an exemplary method as described in Example 4, the polymer stent is first coated with the contrast agent. The stent is subsequently coated with the therapeutic agent or the therapeutic agent in a polymer coating.

In an exemplary embodiment, iohexol, a type of iodinated contrast media, is used as the radiopaque material. As seen in Example 5, iohexol was incorporated in poly(L-lactic acid) (PLLA) polymers and coated on a stent. These stents remained radiopaque after exposure to water at thirty seconds and two minutes.

B. Active Pharmaceutical Ingredients

The stent of the present invention may also be used to deliver one or more APIs. These agents may be released from the stent in desired sequence and with controllable timing in order to have a desired effect on host cell responses. Various types of APIs may be mixed with the polymer solution at desired weight percentages from 0.1 wt % to 55 wt %. The present stents are manufactured without the extreme heating needed for polymer extrusion methods, thus decreasing the likelihood of heat inactivation of any temperature-sensitive therapeutic agents. In an embodiment, the biodegradable polymer is admixed with one or more of a variety of APIs or therapeutic agents. In other embodiment, the API's may be deposited on the fiber surface or into the lumen of the hollow fibers alone or in combination with APIs admixed in the stent polymer. It will be appreciated that by adding a fluoroscopic impermeable agent at the time of spinning the fibers or assembling the stents, the status of the introduced luminal stent may be observed with conventional fluoroscopic equipment. Non-limiting examples of therapeutic agents useful with the present stent include anti-restenosis drugs, anti-proliferative drugs, immunosuppressive compounds, anti-thrombogenic drugs, anti-fibrotic/fibrinolytic compounds, and cytotoxic compounds. In preferred embodiments the agents are anti-restenosis, anti-proliferative drugs such as rapamycin (sirolimus), everolimus, paclitaxel, zotarolimus, Biolimus A9®, pimecrolimus and tacrolimus, anti-thrombogenetic/anti-coagulate drugs such as heparin/enoxaparin/low-molecular-weight heparin, hirudin/bivalirudin/lepirudin/recombinant hirudin, aprotinin, clopidogrel, prasugrel, argatroban, anti-fibrotic or fibrinolytic drugs such as tranilast, colchicine, streptokinase, two-chain urokinase-type (tcu-plasminogen activator, urokinase), tissue-type plasminogen activator PA (t-PA), and single-chain urokinase-type PA (scu-plasminogen activator). If the polymer is biodegradable, in addition to release of the drug through the process of diffusion, the API may also be released as the polymer degrades or resolves, making the agent more readily available to the surrounding tissue environment. When biodegradable polymers are used as drug delivery coatings, porosity is variously disclosed to aid tissue ingrowth, make the erosion of the polymer more predictable, and/or to regulate or enhance the rate of drug release, as, for example, disclosed in U.S. Pat. Nos. 6,099, 562, 5,873,904, 5,342,348, 5,707,385, 5,824,048, 5,527,337, 5,306,286, and 6,013,853.

C. Mechanical Strength

The present stent has not only structural benefits to the stent, and thus to the patient, but also allows the stent to be manufactured with less polymer material, which has advantages of cost as well as of decreasing the exposure of the patient to foreign material. The enhanced mechanical strength is provided via highly oriented polymer molecules.

Figure 5:
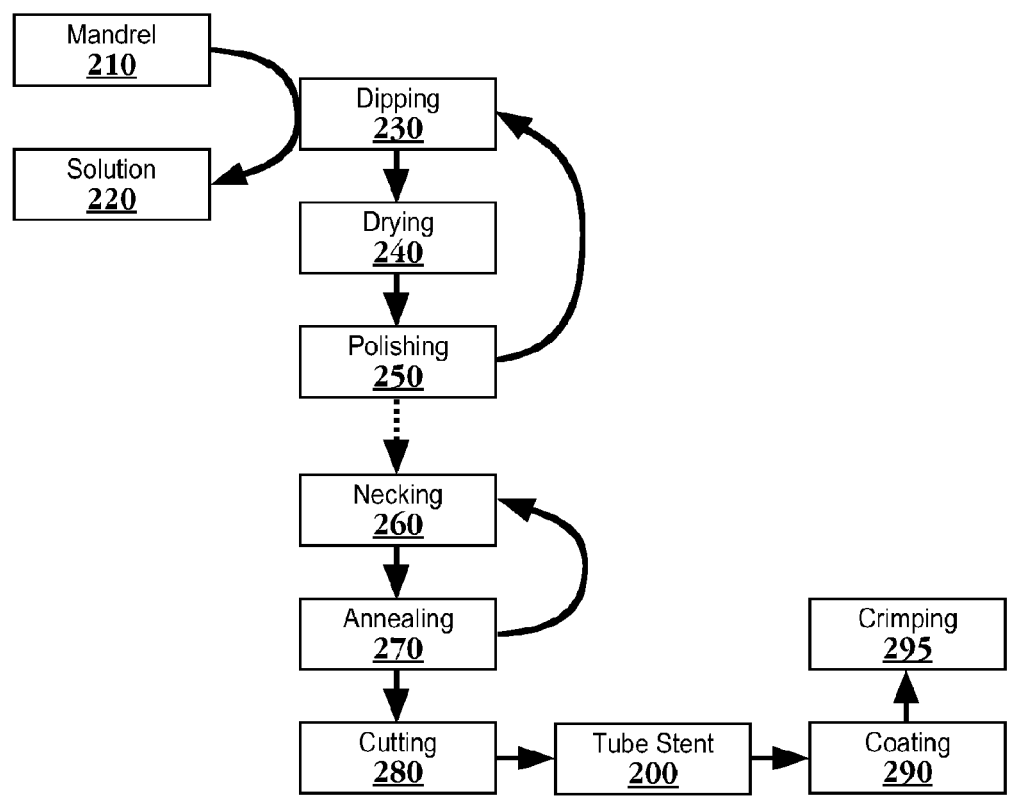
FIG. 5 is a plan illustration of a process for manufacturing a tube stent.
Figure 6:
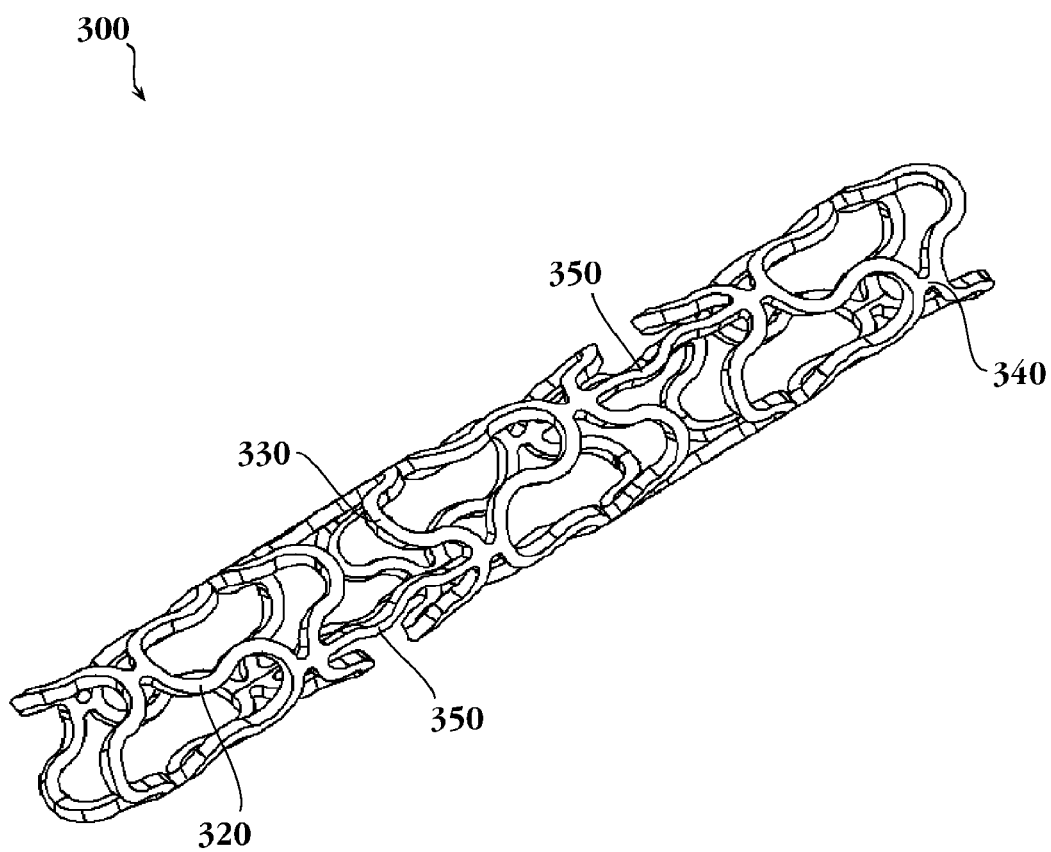
FIG. 6 is a perspective illustration of the three-dimensional structure of an expanded tube stent with a circumferential restraint mechanism facing opposite of the crown valleys.
Figure 7:
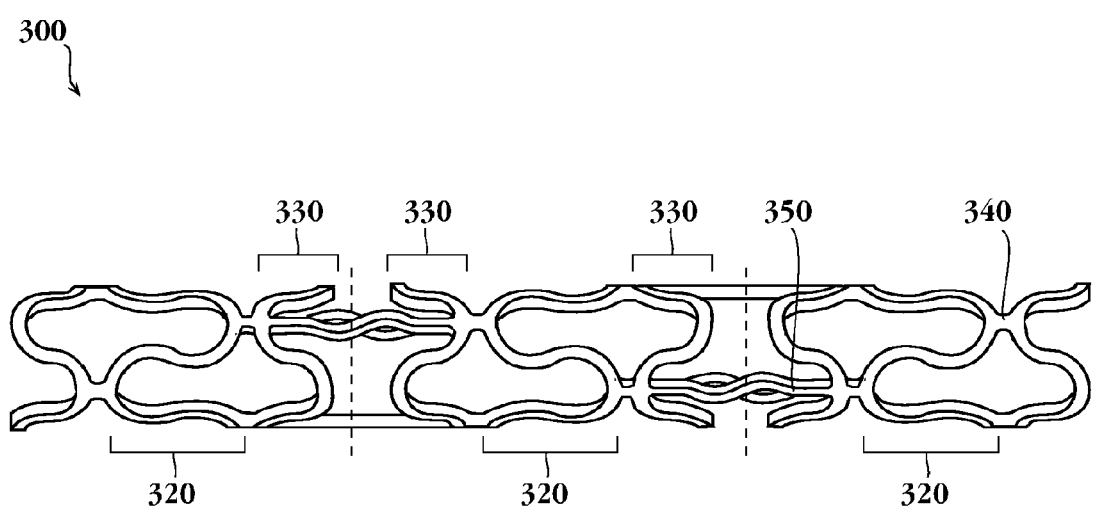
FIG. 7 is a side illustration of the tube stent of FIG. 6.

As described further below and depicted in FIG. 5, the tube stents may be formed by a process for making a polymer stent with enhanced mechanical strength. The process includes the spin drying 240 and necking 260 steps that orient the polymer chains of the tube in the radial and axial directions, respectively. Furthermore, the steps of the process involve do not require extreme heating that is necessary for heat extrusion techniques typically used to form stents. The moderate manufacturing temperature conveys advantages especially where a temperature sensitive API is to be delivered via biodegradable tube stent 200. For example, heat extrusion typically used to manufacture polymer stents must be performed at temperatures above the melting temperature ($T_m$) of the polymer, which in the case of the polymer poly-L-lactic acid is approximately 173° C. In contrast, the necking 260 process of the present invention is carried out at a temperature between the glass transition temperature ($T_g$) and the $T_m$, or approximately 55° to 60° C. for poly-L-lactic acid, and the manufacturing steps which precede the necking 260 step are carried out at room temperature.

It will be appreciated that the fibers of the fiber stent may also be formed by this process. In another embodiment, the mechanical strength of the fiber stent may be enhanced by the configuration of the fibers, described further below, and/or by the manufacturing process.

D. Buffers

The stent of the present invention may further be manufactured in such a way that the stent resorption rate can be controlled. In one embodiment, this is accomplished by addition of buffer salts to alter the stent resorption rate. In this embodiment, one or more buffers, including but not limited to, a phosphate buffer salt, a citrate buffer salt, or NaCl buffer may be loaded in the polymer solution alone or in conjunction with one or more APIs in order to adjust the degradation of the polymer, and thus, the stent. Without being limited as to theory, it is thought that the buffer that is incorporated into the polymer quickly diffuses out of the stent once the stent contacts fluid, thus creating microscopic holes or channels. Water molecules can then permeate the stent through those holes or channels. For example, PLLA polymer decomposition is hydrolysis-driven and subject to the influence of water content. Resorption of the polymer occurs when the long molecular chain is broken down into many single molecules forming lactic acid and then nearby cells uptake the lactic acid. Thus, controlling the amount of buffer powders loaded into the polymer solution, the buffer salt diffusion rate and the stent resorption rate are controllable.

Figure 12:
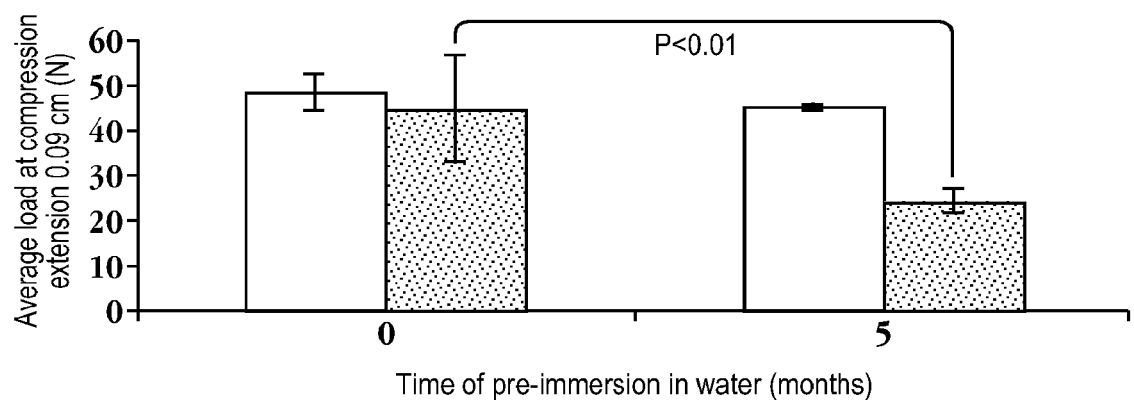
FIG. 12 is a table graph comparing the compression extension as measured by the average load at compression extension (cm (N)) of pure PLLA (■) and phosphate salt containing PLLA (□) tubes at 0 and 5 months of pre-immersion in water.

The concentration of buffer salt is generally from about 0.01% to 15% wt % of the stent; preferably 0.01% to 10% wt %; more preferably 2% to 8% wt %. As described in Example 1, a polymer stent was formed of PLLA with 6% by weight phosphate salt. Referring to FIG. 12, the PLLA tube stent with phosphate salt buffer at 6% wt % resulted in a substantially faster degradation measured at five months as compared to a PLLA tube stent without buffer.

E. Stent Geometry

1. Fiber Stent

FIG. 1 shows a fiber stent 100 constructed in accordance with the invention made from one or more polymer fibers. Preferably, the fiber stent is a luminal stent consisting of a tubular member produced by "knitting" a biodegradable polymer yarn, fiber, or cord. Such a fiber stent is preferably deployed from a luminal stent deployment device comprising the luminal stent which is fitted over a balloon forming portion in the vicinity of a distal end of a delivery catheter.

In a preferred embodiment, the fibers are "biodegradable fibers" that can be decomposed and resorbed by tissues. The fibers can be solid, hollow, or a combination of solid and hollow. Preferably, the fibers are decomposed within about 1 to 60 months after insertion into the body, more preferably in about 3 to 15 months, even more preferably in about 6 to 12 months. The biodegradable fibers may be formed of biodegradable materials as described above. In a preferred embodiment, the polymer fibers are formed of PLLA. In a non-limiting embodiment, these fibers are generally a filament thread of about 5 to about 1,000 μm in diameter. Preferably, the filament thread is sized such that a stent composed of these fibers is firm enough to easily maintain a cylindrical form. Monofilament threads are particularly preferred for use herein. The mean molecular weight of preferred biodegradable polymers is between about 10,000 to about 800,000 DA. It will be appreciated that selection of the biodegradable polymer may depend on the total radial strength necessary to support various sized vessel lumen. The polymer fiber may be formed by any suitable means. In one embodiment, the polymer fiber is formed by thermal extrusion as known in the art. In another embodiment, the fiber is formed by the method as described above and illustrated in FIG. 5.

It will be appreciated that at least some of the stent's polymer fibers may be admixed with one or more APIs as described above. It will further be appreciated that at least some of the polymer fibers may be coated with one or more APIs.

In some embodiments, the polymer fibers used for the stent fabrication are loaded with a non-steroid type anti-inflammation agent, such as turmeric alone or in combination with further API(s). The turmeric-loaded fibers significantly reduce inflammation at the stent implant site by reducing the adhesion of inflammatory cells. The impregnated or coated APIs can be prepared in doses that are controllably delivered over a predetermined time period.

Furthermore, by taking advantage of the fact that the fiber stent produced from biodegradable polymer fibers fully degrades after a predetermined time from the site into which it has been introduced, carcinostatics or anti-thrombotic agents may be mixed into or attached to the fibers for concentrated administration of these agents to the site of lesion.

The fiber stent of the present invention provides adequate mechanical support for the vessel lumen following the interventional procedure. Further, the fiber stent, by being absorbed over controllable periods of time, avoids chronic mechanical disturbance of the vessel wall. The residual stress against the vessel wall is eliminated while the stent is hydrolyzed and the fibers are endothelialized. The fiber stent APIs are released in a controlled fashion during hydrolysis and effective concentrations at target lesions are maintained.

The fiber stent may be introduced into and placed at the site of angioplasty by a catheter fitted with a balloon and deployed by dilating the balloon or any other method as known in the art. The fiber stent may retain its shape for several weeks to several months, usually about 2 months to about 2 years, after placement and hydrolyze in several months, usually about 6-12 months. It will be appreciated that the stent may hydrolyze over a longer period of time such as 2 years.

The methods of using the fiber stent are intended to provide structural support and, optionally, local drug administration to the interior of a body lumen. In one embodiment, the methods are designed to minimize the risk and/or extent of restenosis in a patient who has received localized vascular injury, or who is at risk of vascular occlusion. Typically the vascular injury is produced during an angiographic procedure to open a partially occluded vessel, such as a coronary or peripheral vascular artery. In the angiographic procedure, a balloon catheter is placed at the occlusion site, and a distal-end balloon is inflated and deflated one or more times to force the occluded vessel open. This vessel expansion, particularly involving surface trauma at the vessel wall where plaque may be dislodged, often produces enough localized injury that the vessel responds over time by inflammation, smooth muscle cell proliferation leading to positive remodeling, and reocclusion. Not surprisingly, the occurrence or severity of this process, known as restenosis, is often related to the extent of vessel stretching and injury produced by the angiographic procedure. Particularly where overstretching is 35% or more, restenosis occurs with high frequency and often with substantial severity, i.e., vascular occlusion.

The fiber stent is typically placed in its contracted state typically at the distal end of a catheter, either within the catheter lumen, or in a contracted state on a distal end balloon.

The distal catheter end is then guided to the injury site, or the site of potential occlusion, and released from the catheter, e.g., by using a trip wire to release the stent into the site if the stent is self-expanding, or by expanding the stent on a balloon by balloon inflation, until the stent contacts the vessel walls, in effect, implanting the stent into the tissue wall at the site.

FIGS. 1-4 show an exemplary fiber stent. Referring now to FIG. 1, the fiber stent 100 is comprised of coiled fiber material. The fiber material is a polymer fiber or ply of multiple polymer fibers as described above. Preferably, the polymer comprises PLLA. The use of PLLA to construct the fiber stent is advantageous because it is biodegradable. The degradation mechanism of the fiber stent is generally via hydrolysis at the ester bonds. Degradation may occur over a period of about three months to three years, depending on several factors, in particular, the molecular weight of the polymer and the type of buffer employed. PLLA is also advantageous because it may be impregnated and/or coated with drugs or other therapeutic agents for local treatment of tissue at the stent implant site. It will be appreciated that other biodegradable polymers will have the advantages as described for PLLA.

The fiber material is coiled to form at least one large central lobe 160 that is further comprised of a plurality of peripheral lobes 180 within the large central lobe 160 and connecting segments 130 disposed between the peripheral lobes 180. In a preferred embodiment, the plurality of peripheral lobes comprises at least three peripheral lobes per central lobe. In an alternative configuration, the peripheral lobes 180 may be disposed on the abluminal side of the large central lobe 160 (not shown). The arbitrary bands 120 define the putative starting and ending point of each of the peripheral lobes 180. The large central lobes 160 form the super structure of the fiber stent 100. At least three longitudinal rods 170 are attached on the abluminal surface of the large central lobes 160, preferably using a viscous PLLA-chloroform solution. The longitudinal rods 170 may be composed of the same material as the large central lobes 160 and peripheral lobes 180. In the embodiment shown in FIG. 1, the stent comprises nine central lobes 160 formed of three peripheral lobes 180 linked by connecting bands 130. The peripheral lobes are disposed on the luminal side of the central lobe. The stent further comprises at least one longitudinal or reinforcing rod 170 disposed on the abluminal surface of the fiber stent. Preferably two or more longitudinal rods are disposed on the abluminal surface of the fiber stent. More preferably, three or more longitudinal rods are disposed on the abluminal surface of the fiber stent. The longitudinal may be attached to one or more of the central lobes at multiple points along the stent. As seen in the figure, the central lobes are approximately the same size and are arranged in succession at spaced intervals to define the stent longitudinal axis. Each central lobe has a leading end 162 and a trailing end (not shown). Except for the first and last central lobes, the trailing end of each central lobe is connected to the leading end of the next successive central lobe. It will be appreciated that the stent may be formed of a continuous fiber where the trailing end of each central lobe leads continuously into the leading end of the next successive central lobe. As further seen in the figure, the peripheral lobes may be regularly or substantially regularly spaced about the circumference of the central lobe. In another embodiment, the peripheral lobes may be irregularly spaced about the circumference of the central lobe (not shown). The plurality of peripheral lobes further includes a leading peripheral lobe following the central lobe leading end and a trailing peripheral lobe prior to the central lobe trailing end. One or more additional peripheral lobes may further be positioned between the leading and trailing peripheral lobes. Preferably, the leading peripheral lobe adjoins the leading end of the central lobe and the trailing peripheral lobe adjoins the trailing end of the central lobe.

Figure 2:
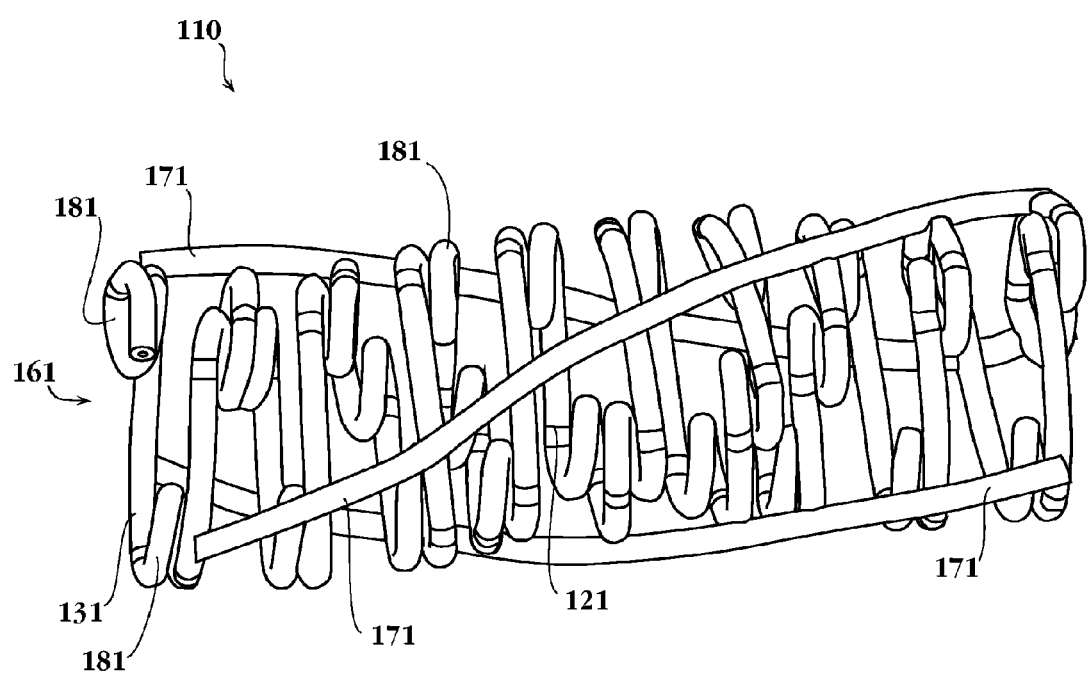
FIG. 2 is a perspective illustration of a side view of the fiber stent of FIG. 1.
Figure 3:
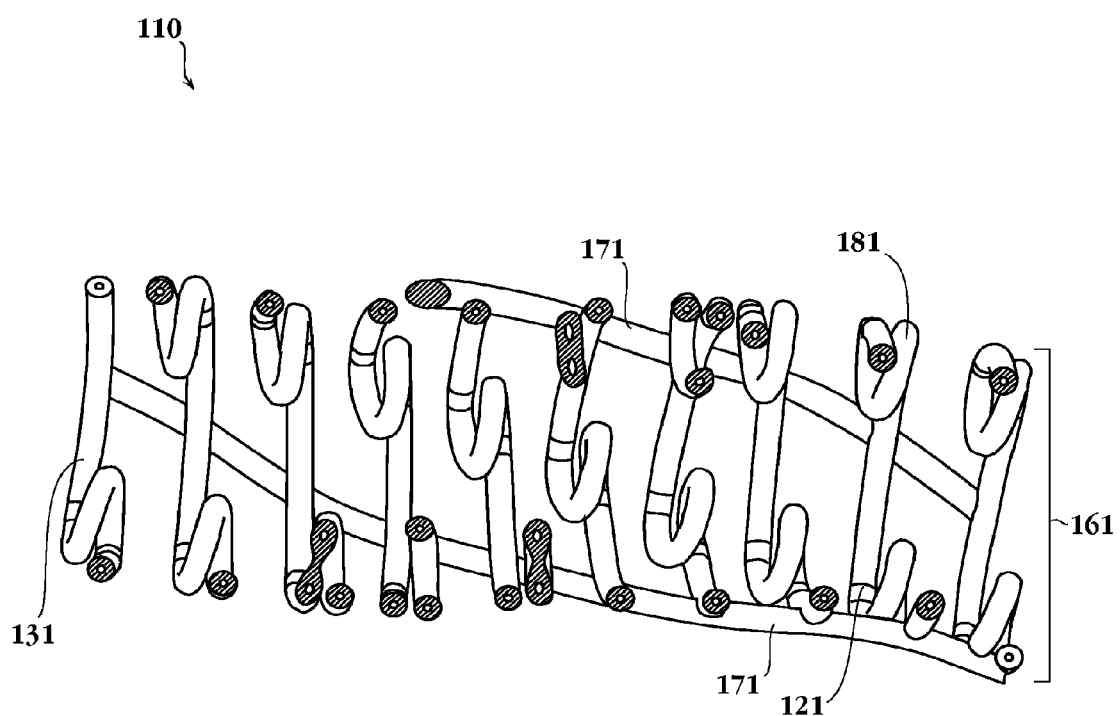
FIG. 3 is a cross-sectional side illustration of the fiber stent of FIG. 1.
Figure 4:
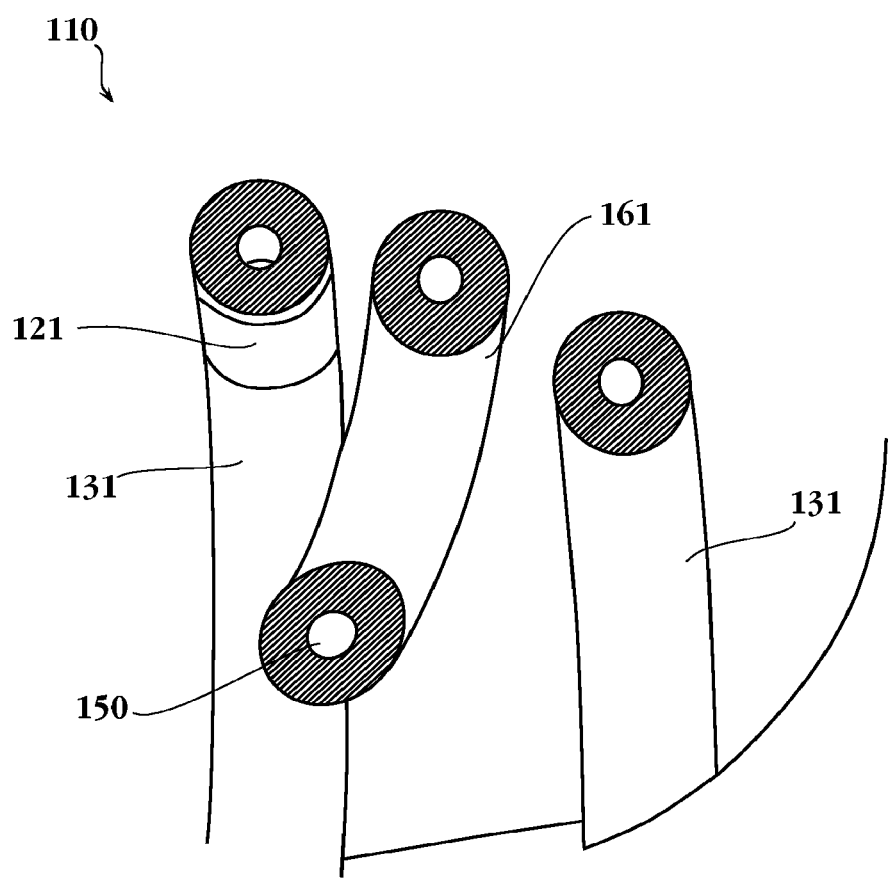
FIG. 4 is an enlarged cross-sectional illustration of the fiber stent of FIG. 1.

FIGS. 2-4 illustrate an alternative embodiment poly-layered fiber stent 110 wherein, the large central lobes 161, peripheral lobes 181, and the longitudinal rods 171 may comprise a multiple-fiber ply material. For example, the large central lobes 161 and peripheral lobes 181 may be formed from a double-fiber or higher ply material, and each of the at least three longitudinal rods 171 may be formed from a triple-fiber ply material for added rigidity. Further, the poly-layered fiber stent 110 may have a hollow lumen 150 that is capable of storing APIs for release after implantation.

Also, by way of example, the length of a preferred embodiment is 18 mm and the initial diameter is 1.9 mm. In this embodiment, the final diameter, after balloon expansion, is preferably about 3.25 mm. Preferably, the stent length is about 8 mm to about 30 mm. In some embodiments, the stent length is up to about 60 mm. Typical coronary artery diameters are about 2 mm to about 4 mm and the expanded diameter of coronary stents is generally suitably dimensioned. It will be appreciated that other body lumens can have diameters up to about 1 cm and stents for these lumens have a suitable expanded diameter. The length of the fiber stent 110 can be increased by increasing the number of large central lobes 161 and peripheral lobes 181. The peripheral lobe 181 and large central lobe 181 diameters may be adjusted to set the final diameter of the stent. For example, coronary stents commercially available have a final expanded diameter range of 2-5 mm. It will be appreciated that the stent may be appropriately sized for the lumen and/or application.

In practicing the present invention, the stent is placed in its contracted state where the central lobes of the stent are in a furled, small diameter state. The stent is typically at the distal end of a catheter, either within the catheter lumen, or in a contracted state on a distal end balloon. The distal catheter end is then guided to the injury site, or the site of potential occlusion, and released from the catheter, e.g., by using a trip wire to release the stent into the site, if the stent is self-expanding, or by expanding the stent on a balloon by balloon inflation, until the stent contacts the vessel walls, in effect, implanting the stent into the tissue wall at the site.

Once deployed at the site, the stent begins to release active compound into the cells lining the vascular site, to inhibit cellular proliferation.

2. Tube Stent

In another embodiment, the stent is a biodegradable polymer tube stent. Typically, the stent is formed in a cylindrical sheet according to the process as illustrated in FIG. 5. Designs may be laser cut 280 from the tubes using excimer laser technology with a wavelength of less than about 310 nm.

The biodegradable polymer tube is built layer by layer on a mandrel 210. Typically, the mandrel is a Teflon® mandrel or Teflon®-coated metal mandrel. It will be appreciated that other mandrels or structures that support the stent form can be used. A biodegradable polymer solution 220 is made by dissolving the biodegradable polymer resins in a suitable solvent, such as (but not limited to) chloroform or dioxane. The solution viscosity is generally from about 1 to about 2000 centipoise; preferably from about 10 to about 500 centipoise.

Buffers such as phosphate buffer or citrate buffer salts may be loaded in the polymer solution alone or in conjunction with one or more APIs. Other biocompatible buffered salts are readily known to those in the medical art, including, but not limited to Ringers solution and lactose.

The tube stent is formed by dip coating 230 the mandrel into the biodegradable polymer solution one or more times until the polymer coating is a desired thickness. The dip 230 coating speed generally ranges from about 1 millimeter/minute to about 10 meter/minute. A typical speed range is from 1 meter/minute to 5 meter/minute. The coated mandrel is then dried 240. Preferably, the coated mandrel is spin dried 240 around the longitudinal axis of the mandrel in a laminar flow hood, leaving a thin polymer layer upon evaporation of solvent. The speed of spin drying 240 can be from about 1 to about 100,000 rpm with a typical range being from about 100 to about 4000 rpm. The spin drying 240 step enhances the radial strength of the polymer tubing via circumferential orientation. The orientation of the spin in the drying step 240 may be repeated in one direction or the orientation may alternate, for instance from the clockwise direction to the counterclockwise direction. This polymer layer is then solvent polished 250 and dried 240 one or more times, leaving behind a layer of thin and smooth polymer tubing (not shown). Preferably, solvent polishing 250 uses pure solvent, which can be the same or different from the solvent used for preparing the polymer solution 220. A typical solvent is chloroform. The whole cycle, including dip 230 coating, spin drying 240 and solvent polishing 250, is preferably performed at or about room temperature (from 10° C. to 30° C.). However, it will be appreciated that a temperature range of about −20° C. to 80° C. is possible. The cycle of dipping, drying, and polishing is preferably repeated in order to increase the thickness of the tubing until a desired thickness, 0.0875 millimeter to 1.25 millimeter, for example, is reached. In one embodiment, the cycle is repeated until at least about 46 layers of polymer are laid down to form a complete tube. As described above, the various cycles need not be conducted with equivalent polymer solutions 220. The polymer, buffer and/or the API may be varied in nature or concentration from layer to layer, as illustrated above with sequential dip 230 coatings.

The polymer tubing may be mechanically strengthened even further by necking 260 and annealing 270 processes. In the necking 260 treatment, the outer diameter thickness of the tubing is reduced as the tubing is drawn through necking dies (not shown), while the inner diameter remains constant. This necking 260 process enhances the axial strength of the tubing by aligning the polymeric molecules along the longitudinal axis. The necking 260 process takes place at a temperature above $T_g$, the polymer's glass transition temperature, and below $T_m$, the polymer's melting temperature. For example, the necking temperature for poly L-lactic acid is approximately 55° C. to 60° C. The necked tube is then annealed 270 by blowing air onto the surface of the necked tube once it comes out of the necking die. The necking 260 and annealing 270 may be repeated until the desired tube outer diameter is achieved.

It will be appreciated that the area drawn down ratio in the necking 260 step affects the strengthening effect. The area drawn down ratio can be from about 1.01 to about 20.00, preferable 3.5 to 6.0. The area drawn down ratio is calculated as follows:

X is the diameter of the polymer-coated mandrel before necking;

Y is the diameter of the mandrel;

Z is the diameter of the polymer-coated mandrel after necking.

$$\text{The area drawn down ratio} (R) = \frac{X^2 - Y^2}{Z^2 - Y^2}$$

Following necking 260, the tube is typically annealed 270 with pure inert gases. Suitable inert gases include, but are not limited to, nitrogen, argon, neon, helium, or other noble gas. Annealing 270 also increases the mechanical strength, by increasing the crystallinity of the polymer and also regulates access of water for hydrolysis.

Tube stents formed by this method had significantly enhanced mechanical strength as compared to convention thermal extruded tube stents. The maximum load at break for thermal extruded poly(L-lactic acid) (PLLA) tube with a wall thickness 0.007" was 46.33±1.66 NT. For tubes of same specifications that were made by the present method had maximum load of 153.13±1.66 NT.

In general, the strength of tube stents decreases as the hydrolysis initiates. For example, PLLA becomes weaker as the hydrolysis rate increases. In the compression extension comparison test as described in Example 1, PLLA containing phosphate salt and pure PLLA specimens were first immersed in water for 5 months and tested for the radial strength. FIG. 12 shows the degraded phosphate salt containing PLLA tube was 49.8% weaker than degraded pure PLLA tube. FIG. 12 indicates that phosphate salt containing PLLA tubes are subject to faster hydrolysis that led to the accelerated loss of radial strength.

In an alternative embodiment, the method of making the polymer tube stent with enhanced mechanical strength includes a repeated dip-coating process 230, necking 260 the polymer tube at a temperature above the glass transition temperature of the polymer and below the melting temperature of the polymer, annealing 270 the polymer tube and excimer laser cutting a stent of desired design from the polymer tube, and finally cut 280 to form a circumferential restraint when expanded.

Figure 8:
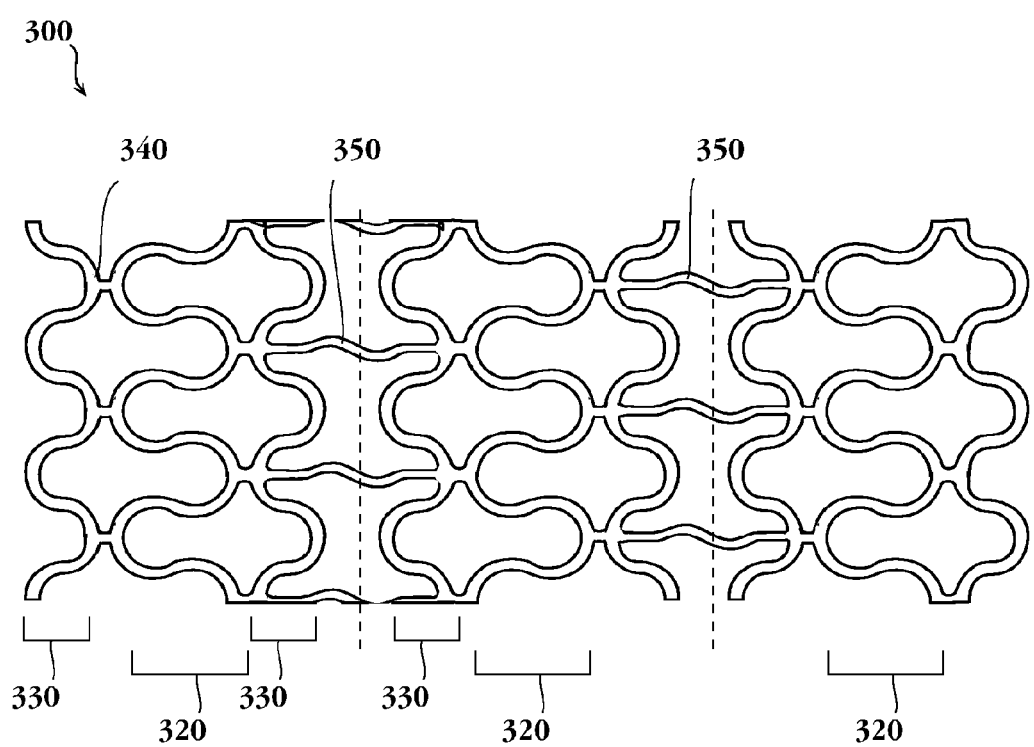
FIG. 8 is a plan illustration showing an enlargement of the tube stent of FIG. 6.
Figure 9:
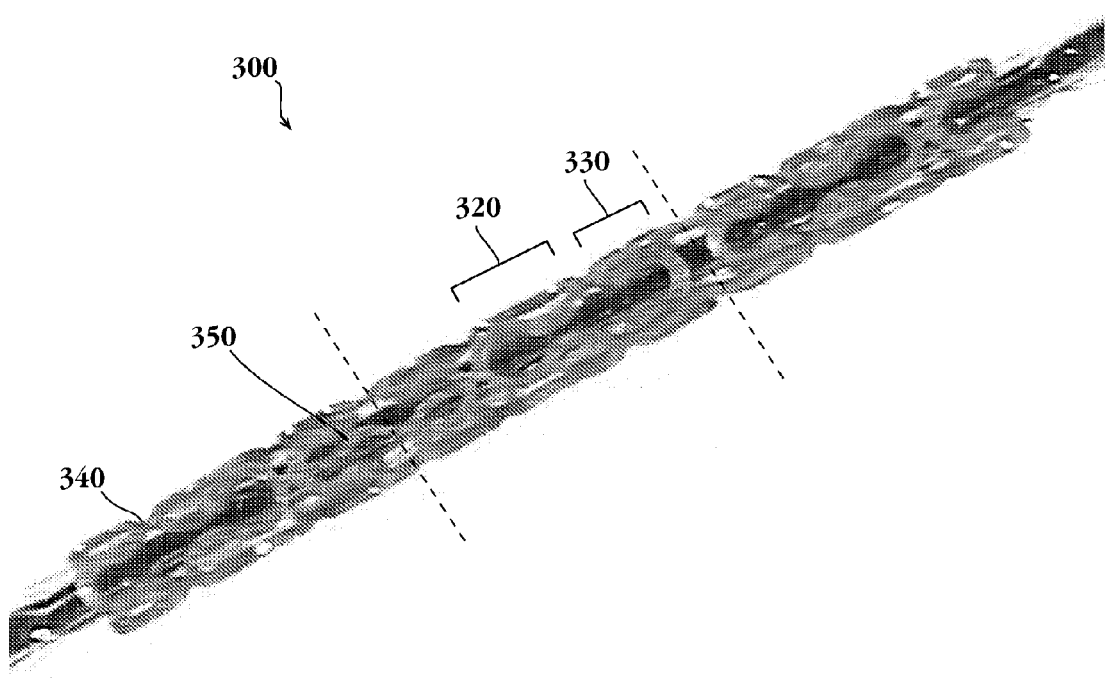
FIG. 9 is a scanned image of a tube stent that is crimped onto a balloon catheter.
Figure 10:
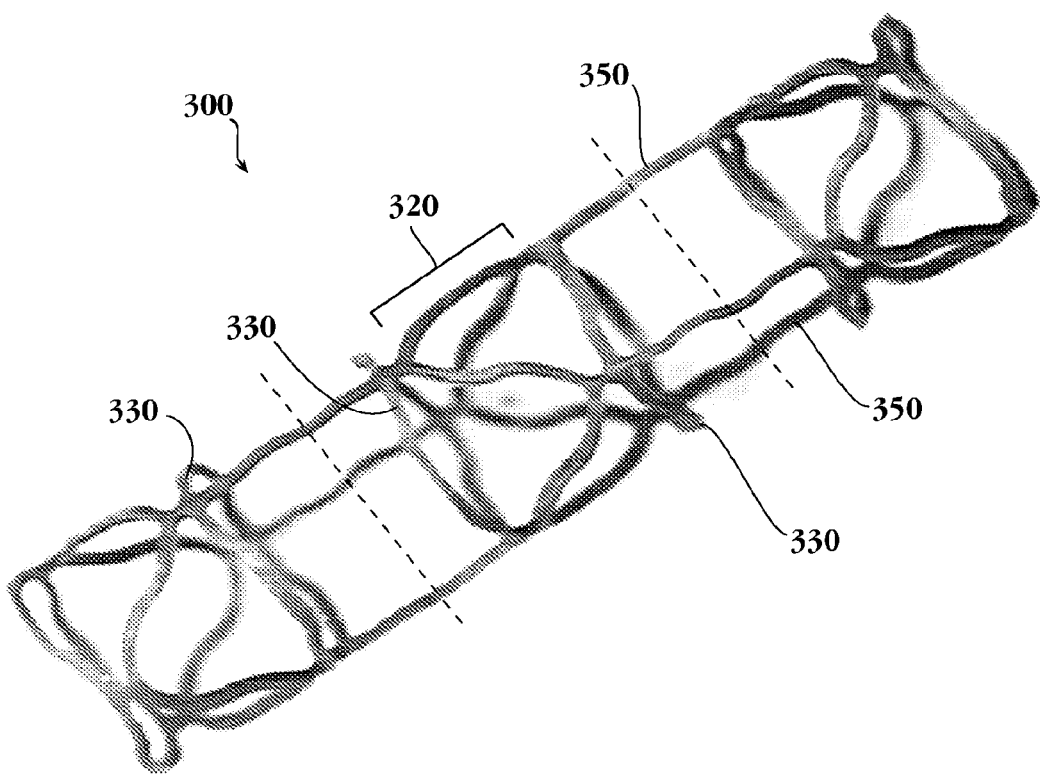
FIG. 10 is a scanned image of a tube stent in an expanded state.

As seen in FIG. 8, the polymer tube stent 300 of the instant invention comprises a sinusoidal strut band 320 and a circumferential restraint band 330. Adjacent bands are connected by either a fixed axial link 340 or flexible axial link 350. As is shown in FIG. 9, two adjacent radially expandable circumferential restraint bands 330 are linked together at their respective valleys by flexible axial link 350. The sinusoidal strut band 320 is linked to the circumferential restraint band 330 at their respective crowns via the fixed axial link 340. The sinusoidal strut band comprises a substantially sinusoidal wave structure with at least one peak and valley around the circumference of the stent. Preferably, the sinusoidal strut band includes more than one peak and valley around the circumference of the stent. During expansion of the polymer tube stent 300 from the unexpanded to the expanded state, the radially expandable circumferential restraint band 330 straightens out to compensate for the increase in radial diameter. As is shown in FIG. 10, the radially expandable circumferential restraint 330 is straightened out to form a complete hoop that will contact the vessel lumen. When the radially expandable circumferential restraint band 330 is straightened out, it locks the polymer tube stent 300 in the expanded state. The polymer tube stent 300 of the present invention may have as few as four peaks per circumference, thus increasing the radius of the bend of each band 330, 340 or as many as twelve peaks or more to accommodate larger vessel lumens. The number of peaks on bands 330, 340 may be adjusted to reduce mechanical stress and strain levels in the bands, particularly during deployment.

In another embodiment, the stent comprises one or more strength modules comprising one or more radially expandable tubular elements. Preferably the radially expandable tubular elements comprise a substantially sinusoidal wave structure of at least one crown peak and crown valley. In one embodiment, the expandable tubular elements have four or fewer crown peaks. The strength modules are interconnected by one or more axial linking elements that add flexibility to the strength module(s). The strength module further has at least two circumferential restraint bands facing opposite of a crown valley of the expandable tubular elements. In an embodiment, the length of the circumferential restraint band restraint band defines the size of the stent when the stent is expanded. In this embodiment, the length of each circumferential restraint band is less than a length of the expandable tubular element.

Figure 11:
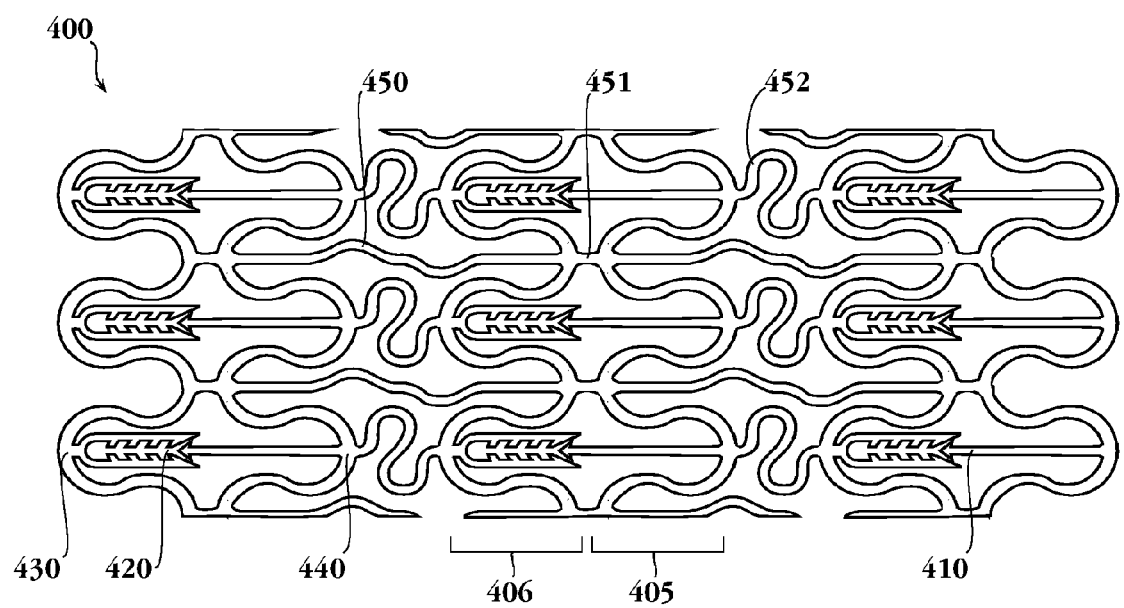
FIG. 11 is a plan illustration of a stent having an axial locking design.

An alternative embodiment, which comprises a biolock polymer stent 400 made of elastic polymer is shown in FIG. 11. The polymer stent 400 is made up of a tubular structure that is made up of one or more radially expandable bands 405, 406 interconnected by long fixed links 450, short fixed links 451, and spring connectors 452 so that the polymer stent 400 is radially expandable between an unexpanded diameter and at least one expanded diameter, with a locking mechanism made up of a first locking member such as an axial peg 410 and a second locking member such as an axial receiver 420. The axial peg 410 protrudes from the valley 430 of band 406, opposite of axial receiver 420 that is attached to the valley 440 of band 405. As the stent is expanded from its unexpanded state to its expanded state, the axial peg 410 makes contact and engages axial receiver 420, locking the stent in its expanded diameter. The locking mechanism is not engaged when the polymer stent 400 is in an unexpanded diameter and is engaged when the tubular structure is in an expanded diameter. The spring connector 452 is disposed between pairs of axial peg 410 and axial receiver 420 to increase radial flexibility.

In some embodiments the polymer stent 400 is lockable at multiple expanded diameters and in some embodiments the locking is irreversible. In one embodiment, the axial peg includes teeth or barbs that are dimensioned to fit within the axial receiver. The axial receiver may further be shaped with one or more positions to house the barbs of the axial peg and hold the axial peg in position. In this manner, the stent can be expanded and locked at one or more positions. It will be appreciated that the stent may originally be locked into a first position and then further be expanded to a second, or any number of, position(s). Thus, the expansion of the stent can be increased and locked into position by the locking of the axial peg and axial receiver. The polymer stent 400 has increased radial strength due to augmented force sharing. The radial force is shared at the interface of the axial peg 410 and the axial receiver 420 in the locking mechanism, rather than on the circumferential strength of the stent struts alone.

The tube stent may also include a mechanism for controlling the resorption rate of the polymer tube and consequently, of the stent. Buffer powders may be incorporated into the polymer solution which is then used to form the tube stent. These buffers quickly diffuse out of the tube stent, once it contacts fluid, thus creating microscopic holes. Water molecules can then permeate the tube stent through those holes. PLLA polymer decomposition is hydrolysis-driven and subject to the influence of water content. Resorption of the polymer occurs when the long molecular chain is broken down into many single molecules forming lactic acid and then nearby cells uptake the lactic acid. Thus, controlling the amount of buffer powders loaded into the polymer solution, the buffer salt diffusion rate and the tube stent resorption rate are controllable.

The tube stent embodiment also optionally includes a process for loading the polymer tubes with multiple APIs or a single API in different concentrations in layered fashion at the time of tube synthesis. Further, it may be desirable to provide different APIs within the different layers of the stent. For example, one may provide an immunosuppressant or anti-restenosis agent in the outer or lateral layer or layers of the stent, an anti-inflammatory agent in the middle layer or layers of the stent, and an anti-thrombogenic agent in the medial (inner) layer or layers of the stent. This is accomplished by changing the drug content in the polymer as various layers of the polymer tube (which will become the stent) are built up through dip coating. The timing and duration of the release kinetics can be tuned by adjusting the sequence of API, buffer, and polymer. Furthermore, as mentioned above, the manufacturing process for the polymer tube stent is carried out at moderate temperatures, which allows use of a much wider range of APIs than is possible with thermally extruded polymers.

Although the invention has been described with respect to particular embodiments and applications, it will be appreciated that various changes and modifications may be made without departing from the invention. The following examples illustrate various aspects of making and using the stent invention herein. They are not intended to limit the scope of the invention.

III. Examples

Materials and Methods

Iohexol was purchased from Amersham (product #0407-1414-80).

Methanol was purchased from EMD (Product #MX0488).

Phosphatidylcholine was purchased from Sigma-Aldrich (PN P3556, 20 mg)

Radiograph images were taken with an OEC Model 9600 ESP C-ARM 60 Hz with a magnification setting of MAG2.

Example 1

Preparation of Biodegradable Polymer Tubes

A biodegradable polymer tube was built layer by layer on a mandrel by dipping the mandrel into a biodegradable polymer solution of 12% wt % PLLA in $CCl_3H$ (chloroform). The mandrel was dipped 46 times in the PLLA solution with a rate of dipping of ~0.1 meter per second.

The coated mandrel was then spin dried around the longitudinal axis in a laminar flow hood, leaving a thin polymer layer upon evaporation of solvent. The spin in the drying step was repeated. The resulting a polymer tube had a thickness of ~0.2 mm and was 6% by weight phosphate salt buffer. This polymer layer was then solvent polished with chloroform or the pure solvent in which the polymer is dissolved and dried, leaving behind a layer of thin and smooth polymer tubing. The outer diameter thickness of the tube stent was reduced by drawing the tube stent through necking dies, while keeping the inner diameter of the stent constant.

Following necking, the tubing was annealed with pure inert nitrogen.

The average load at compression was measured before and after 5 months of immersion in water as measured by a radial force test performed on an Instron (Norwood, Mass.) force delivery/measuring system. The average load at compression for stents with and without buffer was tested with the results shown in FIG. 12.

Example 2

Design and Fabrication of Stent

The stent pattern was designed using CAD software. Flat layout designs and uncut biodegradable polymer tubing were sent to a laser working studio for laser cutting. Several laser cutting facilities are commercially available such as, Resonetics (Nashua, N.H.) and Spectralytics (Dassel, Minn.). Stent designs were cut from biodegradable polymer tube stents with an excimer laser with a wavelength of less than 310 nm.

Those skilled in the art will appreciate that the inventive stents, in the disclosed embodiments or variations thereof, provide mechanical and therapeutic advantages over conventional stents. In addition, advantageous treatments will suggest themselves to the skilled practitioner considering the foregoing description of the inventions. By virtue of the biodegradable polymeric nature of the inventive stents, the same vessel site can be retreated at a later time if needed, including staging procedures during growth of the patient. Similarly, successive treatments of a tissue that is changing size can be facilitated with the disclosed stents. It should also be noted that the inventive stents can be implanted at a site of healthy tissue for diagnostic purposes or therapeutic treatment of adjacent tissue.

Example 3

Radiopaque Stent with Iodinated Contrast Agent

PLLA polymer stents 0.8-1.2 cm long with PLLA fiber diameter of 0.01905 cm and fiber length of 15-22 cm were used. Iohexol was dissolved in methanol to a concentration of 350 mg/mL. The pure iohexol solution was then sprayed onto the top layer of the PLLA stents to a coating thickness of about 0.01". The measured dose on all stent samples was 1000 μg/stent. Once the methanol evaporated, iohexol covered the abluminal stent surface completely. The radiopacity of the coated stent was observed under the c-arm after exposure to water for 30 seconds with the results shown in FIG. 13 (#4). The radiopacity of a control stent formed of pure PLLA was also tested (#1).

Example 4

Stent with BA9-PLLA Coating Solution on Top of Iodinated Contrast Coating to Create Radiopacity PLLA polymer stents 0.8-1.2 cm long with PLLA fiber diameter of 0.01905 cm and fiber length of 15-22 cm were coated with iohexol. The stent characteristics are shown in Table 1.

TABLE 1

| Stent Characteristics | | |
|---|---|---|
| Stent length (cm) | 0.8 | 1.2 |
| Total fiber length (cm) | 15 | 22 |
| Quantity | 1 | 3 |

Iohexol was first dissolved in methanol to a concentration of 350 mg/mL. The pure iohexol solution was then spray-coated onto the PLLA stents. The measured dose on all stent samples was 1000 μg/cm of stent. The BA9-PLLA coating solution was sprayed on top of the iohexol coating to completely cover the abluminal surface. The coated stents were then immersed in water for 30 seconds or two minutes before observation.

TABLE 2

| | Coated stent | | | |
|---|---|---|---|---|
| | Stent | | | |
| | 1 | 2 | 3 | 4 |
| Fiber length (cm) | 16 | 16 | 22 | 23 |
| Bare stent weight (mg) | 2.457 | 2.287 | 2.504 | 2.338 |
| | 2.455 | 2.29 | 2.506 | 2.339 |
| | 2.456 | 2.289 | 2.506 | 2.338 |
| Average | 2.456 | 2.288667 | 2.505333 | 2.338333 |
| Std. Deviation | 0.001 | 0.001528 | 0.00115 | 0.000577 |
| Final iohexol coating weight (mg) | 3.396 | 3.486 | 3.545 | 3.601 |
| | 3.399 | 3.49 | 3.542 | 3.603 |
| | 3.399 | 3.49 | 3.542 | 3.603 |
| Average | 0.942 | 1.2 | 1.037667 | 1.264 |
| Std. Deviation | 0.001732 | 0.002309 | 0.001732 | 0.001155 |
| Estimated iohexol weight % | 0.277222 | 0.343971 | 0.292878 | 0.350884 |
| Final BA9 coating weight (mg) | 3.818 | 4.011 | 3.96 | 4.152 |
| | 3.817 | 4.013 | 3.96 | 4.15 |
| | 3.817 | 4.013 | 3.96 | 4.15 |
| Average | 0.419333 | 0.523667 | 0.417 | 0.548333 |
| Std. Deviation | 0.000577 | 0.001155 | 0 | 0.001155 |
| Estimated BA9 weight (mg) | 0.209667 | 0.261833 | 0.2085 | 0.274167 |

Figure 14:
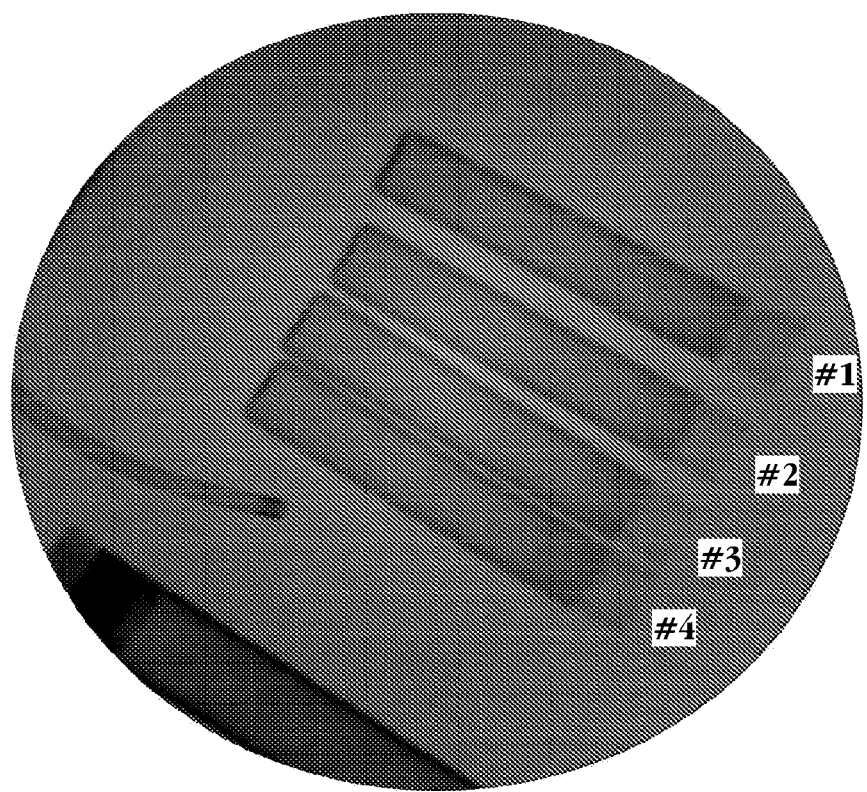
FIG. 14 is a radiograph image of a PLLA stent (#1 and #4), a stent coated with iohexol and BA9-PLLA after 2 minute water immersion (#2) and after 30 seconds of water immersion (#3) and a guiding catheter.

The radiopacity of the coated stents when exposed to water for 30 seconds, two minutes and two control stent formed of pure PLLA were tested and are shown in FIG. 14.

Example 5

Impregnating Stent with Iodinated Contrast Agent to Create Radiopacity

The PLLA backbone of the stent was impregnated with a contrast agent. Iohoxel fine powder was suspended in PLLA-chloroform solution with a final weight of 26 or 50 weight percent of iohexol. In The radiopacity of the stents was observed under the c-arm after exposure to water for 30 seconds with the results shown in FIG. 13 (#2 and #3). The radiopacity of a control stent formed of pure PLLA was also tested (#1). As seen in the figure, radiopacity increased with an increase in iohexol weight percentage.

Although preferred embodiments have been described and illustrated, it should be understood that various changes, substitutions and alterations can be made therein without departing from the spirit and scope of the invention as defined by the appended claims.

Example 6

Hydrophobic Iohexol Coating

A. Preparation of Phosphatidylcholine-Iohexol Liposome

Phosphatidylcholine (PC, available from Sigma-Aldrich, product number P3556, 20 mg) is dissolved in 10 mL chloroform in a 50-ml round-bottom flask with a long extension neck, and the chloroform is then removed under reduced pressure by a rotary evaporator. The system is then purged with nitrogen and PC is re-dissolved in the chloroform to form the solvent phase.

The aqueous phase (50 mg Iohexol in 1 mL distilled water) is then added, the system is kept continuously under nitrogen, and the resulting two-phase system is sonicated briefly (2-5 min) in a bath-type sonicator (Bransonic Ultrasonic Cleaner, 1510R-MTH) until the mixture becomes either a clear one-phase dispersion or a homogeneous opalescent dispersion that does not separate for at least 30 min after sonication. The sonication temperature is 20-25° C. The mixture is then placed on the rotary evaporator and chloroform is removed under reduced pressure (water aspirator) at 20-25° C., rotating at approximately 200 rpm.

During evaporation of chloroform, the system generally froths. As the majority of the solvent is removed, the material first forms a viscous gel and subsequently (within 5-10 min) it becomes an aqueous suspension. At this point excess water can be added (but this is not necessary) and the suspension evaporated for an additional 15 min at 20° C. to remove traces of solvent. The preparation is then centrifuged to remove nonencapsulated iohexol and residual chloroform. Finally, the PC-iohexol liposome remains at 450° C. for at least 30 min to completely remove water. It is estimated 1.7-2.5 mg iohexol per mg PC.

B. Spray Coating of PC-Iohexol onto Biodegradable Stents

PC-iohexol liposome (10 mg) is suspended in (3 ml) ethylene acetate and sonicated for 30 minutes. The solution is then spray-coated onto stents. The spray coating process continues until the net coating weight reaching 1.5 mg per stent. Then stents are vacuum dried for 48 hours to remove ethylene acetate.

Reference: Reverse phase evaporation method. Henze et al, Radio-opaque liposomes for the improved visualization of focal liver disease by computerized tomography. Comput Med Imaging Graph. 1989 November-December; 13(6): 455-62.

We claim:

1. A method of making a polymer stent with enhanced mechanical strength comprising the steps of:
    (a) dip-coating a mandrel with a solution comprising one or more biocompatible polymers to form a polymer tube;
    (b) spin-drying the polymer tube around its longitudinal axis;
    (c) solvent-polishing and vacuum drying the polymer tube;
    (d) repeating steps a-c until the polymer tube reaches a desired thickness;
    (e) necking the polymer tube by drawing the mandrel bearing the polymer tube through one or more necking dies of decreasing diameter, wherein said necking is carried out at a temperature above the glass transition temperature of the polymer and below the melting temperature of the polymer;
    (f) annealing the polymer tube with an inert gas;
    (g) removing the polymer tube from the mandrel; and
    (h) creating a design in said polymer tube.

2. The method of claim 1, wherein said design is created by laser cutting said polymer tube.

3. The method of claim 1, wherein the solution comprising one or more biocompatible polymers also comprises one or more active pharmaceutical ingredients.

4. The method of claim 1, wherein the solution comprising one or more biocompatible polymers is used in all repetitions of the dip-coating step.

5. The method of claim 1, wherein said solution comprising one or more biocompatible polymers comprises at least two solutions and said repeating step comprises dip-coating the mandrel in a different solution in each repetition.

6. The method of claim 1, wherein one or more biocompatible polymers forming the polymer tube includes an iodinated contrast agent.

* * * * *